US00PP23572P3

(12) United States Plant Patent
Bell

(10) Patent No.: US PP23,572 P3
(45) Date of Patent: Apr. 30, 2013

(54) BLUEBERRY PLANT NAMED 'RIDLEY 1111'

(50) Latin Name: ***Vaccinium* hybrid**
Varietal Denomination: Ridley 1111

(75) Inventor: Ridley Bell, Lindendale (AU)

(73) Assignee: Mountain Blue Orchards PTY Ltd., Lindendale (AU)

( * ) Notice: Subject to any disclaimer, the term of this patent is extended or adjusted under 35 U.S.C. 154(b) by 99 days.

(21) Appl. No.: 12/930,887

(22) Filed: Jan. 18, 2011

(65) Prior Publication Data

US 2011/0185459 P1 Jul. 28, 2011

Related U.S. Application Data

(60) Provisional application No. 61/336,459, filed on Jan. 22, 2010.

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

PP11,807 P2 3/2001 Lyrene
PP19,503 P3 11/2008 Lyrene
PP20,695 P2 2/2010 Wright et al.

*Primary Examiner* — June Hwu
(74) *Attorney, Agent, or Firm* — Davis Wright Tremaine LLP; Dale C. Hunt; Wenhua Yu

(57) ABSTRACT

A new and distinct cultivar of *Vaccinium* hybrid plant named 'RIDLEY 1111', characterized by its combination of upright to bushy plant shape and strong plant growth vigor, evergreen foliage, earliness of flowering and fruiting, medium fruit size, firm fruit suited to handling, attractive dark blue fruit color and small picking scar. This combination results in higher quality fruit with an earlier availability than other varieties.

2 Drawing Sheets

Latin name of genus and species of plant claimed: *Vaccinium* hybrid.

Variety denomination: 'Ridley 1111'.

BACKGROUND OF THE INVENTION

The present invention relates to a new and distinct perennial variety of *Vaccinium* hybrid (Southern Highbush Blueberry), which has been given the variety denomination of 'Ridley 1111'. Its market class is that of a fruiting plant. 'Ridley 1111' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in 2001 from open pollinated seed parent 'C99-42' (U.S. Plant Pat. No. 20,695). The new cultivar was discovered and selected as a single plant within a population of plants of *Vaccinium* hybrids in 2003 in a commercial field plantation environment at Lindendale, New South Wales, Australia. Selection criteria was a combination of strong plant growth vigor, low chilling requirement, earliness of flowering and fruiting, firm fruit suited to handling, sweet berries and small picking scar. The selection was subsequently evaluated for a number of years at the commercial at Lindendale, New South Wales, Australia.

Asexual reproduction of the new cultivar by cutting propagation since 2003 at Lindendale, New South Wales, Australia and has demonstrated that the new cultivar reproduces true to type with all of the characteristics, as herein described, firmly fixed and retained through successive generations of such asexual propagation.

The new variety has been primarily compared to the variety 'C99-42' (U.S. Plant Pat. No. 20,695). In Lindendale, New South Wales, Australia the time of fruit ripening of 'Ridley 1111' is classified as 'very early' whereas the time of fruit ripening of 'C99-42' is classified as 'early'. The earlier time of fruit ripening of 'Ridley 1111' allows for a greater period of production on farm and an ability to supply fresh fruit markets at an earlier date than 'C99-42'. The time of beginning of flowering of 'Ridley 1111' is classified as 'very early' whereas the time of beginning of flowering of time of 'C99-42' is classified as 'very early to early'. The leaf width of 'Ridley 1111' is 'medium to broad' (mean 31.3 mm) whereas the leaf width of 'C99-42' is 'narrow to medium' (mean 25.0 mm). The berry diameter of 'Ridley 1111' is medium to large (mean 17.3 mm) whereas the berry diameter of 'C99-42' is 'medium' (mean 15.5 mm). The berry shape of 'Ridley 1111' is oblate whereas the berry shape of 'C99-42' is a round. The berry calyx basin diameter of 'Ridley 1111' is medium to large (mean 6.8 mm) whereas the berry calyx basin diameter of 'C99-42' is 'medium' (mean 5.6 mm). The berry sweetness of 'Ridley 1111' is 'medium to high' whereas 'C99-42' is 'low to medium'. This combination of vegetative and fruiting attributes results in 'Ridley 1111' being a desirable variety for very early season commercial production. See Table 1 for comparisons 'Ridley 1111' can also be compared to the variety 'Jewel' (U.S. Plant Pat. No. 11,807). The plant growth vigour of 'Ridley 1111' is 'strong' whereas the plant growth vigour of 'Jewel' is 'medium to strong'. In Lindendale, New South Wales, Australia the time of fruit ripening of 'Ridley 1111' is classified as 'very early' whereas the time of fruit ripening of 'Jewel' is classified as 'mid-season'. The time of beginning of flowering of 'Ridley 1111' is classified as 'very early' whereas the time of beginning of flowering of time of 'Jewel' is classified as 'early to medium'. The size of the flower's corolla tube of 'Ridley 1111' is 'medium to large' whereas the size of corolla tube of 'Jewel' is 'small to medium'. The berry shape of 'Ridley 1111' is oblate whereas the berry shape of 'Jewel' is a round. The berry calyx basin diameter of 'Ridley 1111' is medium to large (mean 6.8 mm) whereas the berry calyx basin diameter of 'Jewel' is 'medium' (mean 5.7 mm). The berry sweetness of 'Ridley 1111' is 'medium to high' whereas 'Jewel' is 'medium'. The berry acidity of 'Ridley 1111' is 'medium' whereas 'Jewel' is 'high'.

'Ridley 1111' can also be compared to the variety 'Snowchaser' (U.S. Plant Pat. No. 19,503). The plant growth vigour of 'Ridley 1111' is 'strong' whereas the plant growth vigour of 'Snowchaser' is 'medium'. The leaf length of 'Ridley 1111' is 'medium to long' (mean 58.8 mm) whereas the leaf length of 'Snowchaser' is 'long' (mean 63.8 mm). The size of the flower's corolla tube of 'Ridley 1111' is 'medium to large' whereas the size of corolla tube of 'Snowchaser' is 'medium'. The berry shape of 'Ridley 1111' is oblate whereas the berry shape of 'Snowchaser' is a round. The berry calyx basin depth of 'Ridley 1111' is 'medium' whereas the berry calyx basin depth of 'Snowchaser' is 'shallow'.

SUMMARY OF THE INVENTION

The following characteristics of the new cultivar have been repeatedly observed and can be used to distinguish 'RIDLEY 1111' as a new and distinct cultivar of *Vaccinium* hybrid plant:

1. Upright to bushy plant growth habit
2. Very early timing of beginning of flowering
3. Very early timing of fruit ripening
4. Strong plant growth vigour
5. Dark blue berry color
6. Berry firmness is firm
7. Picking scar is dry Plants of the new cultivar differ from plants of the *Vaccinium* hybrid parents primarily in very early to early timing of beginning of flowering and very early to early timing of fruit ripening whereas the parent varieties are early to mid season in these characters.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'RIDLEY 1111'.

DETAILED BOTANICAL DESCRIPTION

Figure 1:
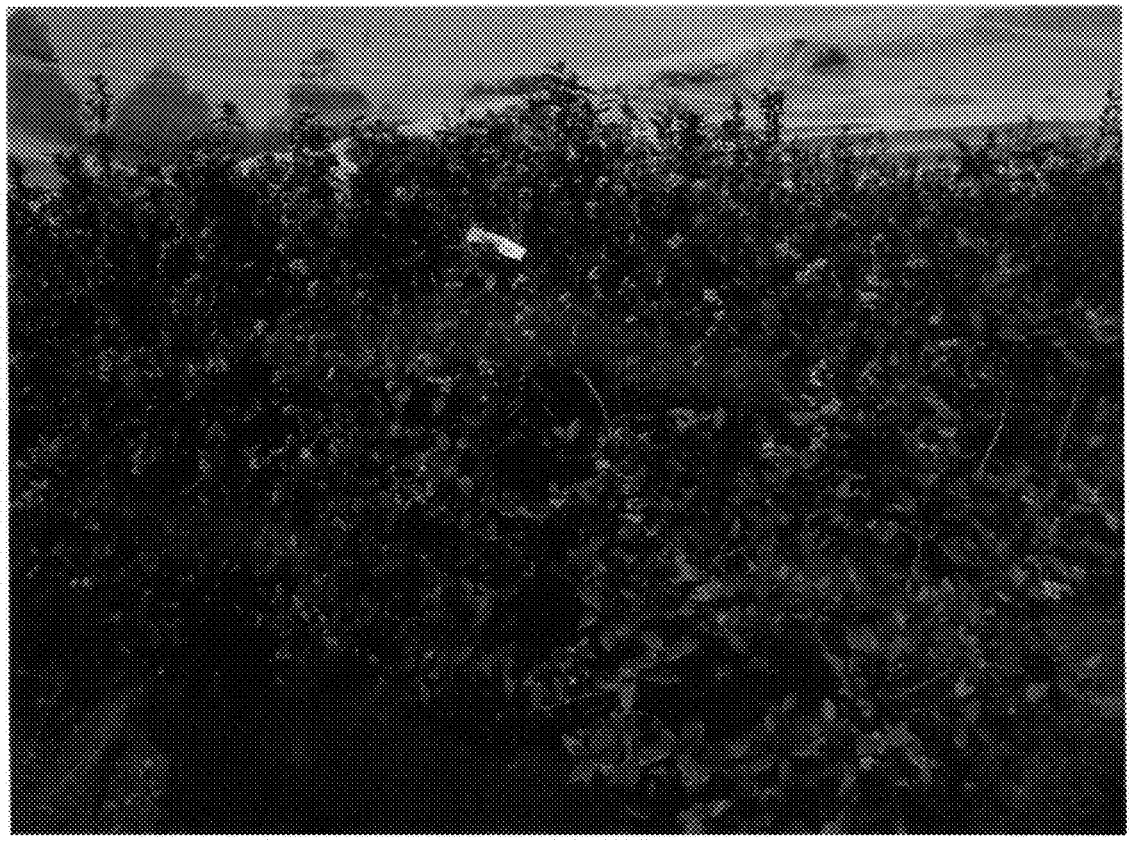
FIG. 1 illustrates a 'RIDLEY 1111' in a commercial field planting.
Figure 2:
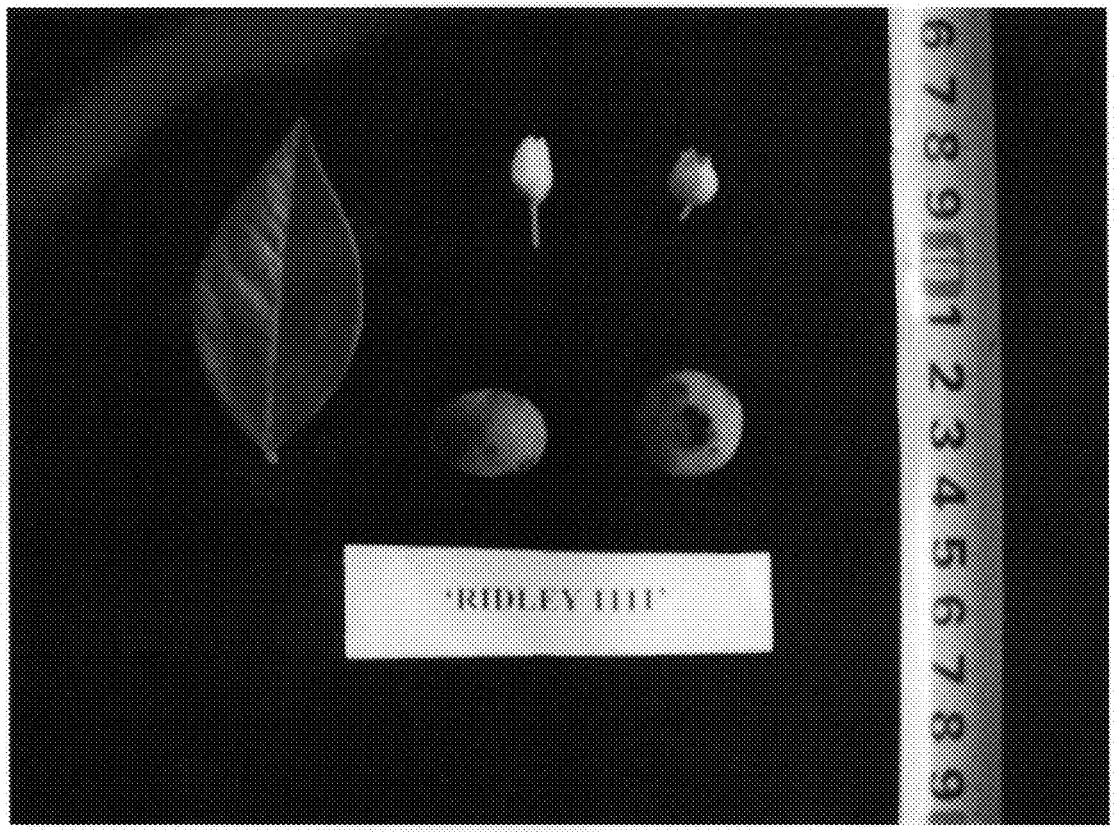
FIG. 2 illustrates a 'RIDLEY 1111' leaf, flower and berry shapes and dimensions.

The following is a detailed botanical description of a new and distinct variety of an *Vaccinium* hybrid ornamental plant known as 'RIDLEY 1111'. Plant observations were made on plants grown in Lindendale, New South Wales, Australia. Unless indicated otherwise, the descriptions disclosed herein are based upon observations made in August 2009 of mature 'RIDLEY 1111' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'RIDLEY 1111' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Vaccinium* hybrid cultivar RIDLEY 1111.

Parentage:

*Parents*.—Seed parent 'C99-42' (U.S. Plant Pat. No. 20,695).

Plant:

*Growth habit*.—Semi-upright and bushy.
*Growth vigor*.—Is strong.
*Plant height*.—Is approximately 2.0 m.
*Plant width*.—Is approximately 1.2 m.
*Flower bud density*.—Is medium.
*Twigginess*.—Is low.
*Time of beginning of flowering*.—Is very early (begins late April to early May; peaks mid July) when grown as an evergreen in Australia.
*Time of fruit ripening*.—Is very early (begins early to mid June; peaks mid September) when grown as an evergreen in Australia.

Stem:

*Suckering tendency*.—Plants typically have 5-7 major canes per plant from a base 30 cm in diameter on 6 year old plants.
*Canes*.—Erect to semi-erect with moderate branching; color greyed orange 198C; 2 year old cane diameter 12 mm, colored greyed orange 177B, some flaking of bark, current season wood diameter 3-4 mm, colored yellow green 144C.
*Internode length on strong, new shoots*.—15-20 mm.
*Fruiting wood*.—Numerous twigs to 10 cm in length.
*Surface texture of new wood*.—Smooth.

Fully developed leaf:

*Length*.—Medium to long 60-70 mm.
*Width*.—Medium to broad approximately 30 mm.
*Shape*.—Elliptic.
*Color of upper surface*.—Yellow green 137A.
*Color of lower surface*.—Yellow green 148C.
*Intensity of color*.—Medium.
*Margin*.—Entire.
*Undulation of margin*.—Weak.
*Pubescence of upper side*.—Absent.
*Pubescence of lower side*.—Absent.
*Cross sectional profile*.—Flat.
*Longitudinal profile*.—Straight.
*Attitude*.—Broad acute to horizontal.
*Shape of apex*.—Is acuminate.
*Shape of base*.—Is obtuse.

Inflorescence:

*Length of peduncle*.—To 12 mm.
*Length of pedicel*.—Long 4-6 mm.
*Number of flowers per cluster*.—Median 7.
*Flower cluster density*.—Is medium-dense.
*Diameter*.—20-35 mm.
*Length*.—30-50 mm.
*Color of peduncle*.—146C.
*Texture of peduncle*.—Is smooth.
*Color of pedicel*.—146C.
*Texture of pedicel*.—Is smooth.

Flowers:

*Length of bud*.—Medium (to 15 mm), bud shape tubular, oblong with acute apex.
*Bud color*.—Green 138A (calyx) with white 155D corolla.
*Length of corolla tube*.—Medium to long (to 15 mm).

*Width of corolla tube*.—Medium to broad (to 11 mm).
*Corolla aperture*.—Diameter 3-4 mm.
*Color of corolla*.—White 155D.
*Anthocyanin coloration of corolla*.—Absent.
*Corolla ridges*.—Present.
*Protusion of stigma*.—Absent.
*Fragrance*.—Weak.
*Shape*.—Urceolate.
*Abundance of pollen*.—High.
*Calyx (with sepals) diameter*.—5-6 mm.
*Calyx color*.—Green 138A.

Productivity: 3 to 4 kg per season from 3-4 year old plants planted at 3.0 m×0.9 m density.

Cold hardiness: RIDLEY 1111 has not been grown in all environments including harsh winter environments. Cold tolerance is expected to be low.

Chilling requirement: RIDLEY 1111 has not been grown in all environments and is typically grown as an evergreen crop where chilling hours are not important. RIDLEY 1111 is classed as 'low chill', typical of Southern Highbush Blueberry varieties with an estimated chilling requirement of 250 hours (not tested).

Leafing: Plants retain leaves year round (at Lindendale, NSW Australia) and RIDLEY 1111 is grown commercially as an evergreen crop. New leafing occurs in mid to late August at Lindendale, NSW Australia.

Fruit:
*Unripe fruit color intensity*.—Light.
*Unripe fruit color*.—144A.
*Cluster density*.—Is dense.
*Diameter*.—Is medium (mean 17.3 mm).
*Weight*.—Medium (approximately 2.1 g).
*Shape*.—Oblate.
*Attitude of calyx*.—Erect.
*Diameter of calyx basin*.—Medium (mean 7 mm).
*Depth of calyx basin*.—Is shallow (to 1.5 mm).
*Intensity of bloom*.—Strong.
*Intensity of blue color of skin with bloom removed*.—Is very dark.
*Color of skin*.—202A.
*Sweetness when ripe*.—Medium to high.
*Color of flesh when ripe*.—Yellow green 145D to yellow green 150D.
*Firmness when ripe*.—Firm.
*Acidity when ripe*.—Medium.
*Size of scar*.—Is small (1.0-1.5 mm).
*Storage quality*.—Good.
*Date of 50% maturity*.—Approximately 15$^{th}$ August at Lindendale, NSW Australia.
*Fruit development period*.—Approximately 55 days in protected cultivation at Lindendale, NSW Australia.

Seed:
*Seed color*.—Greyed orange 165B.
*Seed abundance in fruit*.—Medium.
*Seed size*.—1.6-1.8 mm long for fully developed seeds.

TABLE 1

Comparison with other varieties (extract from Australian PBR data)

| Organ/Plant Part: Context | Ridley 1111 | C99-42 | Jewel | Snowchaser |
|---|---|---|---|---|
| *Plant: vigour | strong | medium | medium to strong | medium |

TABLE 1-continued

Comparison with other varieties (extract from Australian PBR data)

| Organ/Plant Part: Context | Ridley 1111 | C99-42 | Jewel | Snowchaser |
|---|---|---|---|---|
| *Plant: growth habit | semi upright | semi upright | semi upright | semi upright |
| *Leaf: length | medium to long | medium | medium | long |
| Leaf: width | medium to broad | narrow to medium | medium | broad |
| *Leaf: shape | elliptic | elliptic | elliptic | elliptic |
| Leaf: colour of upper side | green | green | green | green |
| *Leaf: intensity of green colour on upper side (varieties with green leaf colour only) | medium | medium | light | medium |
| *Leaf: margin | entire | entire | entire | entire |
| *Flower: size of corolla tube | medium to large | medium | small to medium | medium |
| *Flower: anthocyanin colouration of corolla tube | absent or very weak | absent or very weak | absent or very weak | absent or very weak |
| Flower: ridges on corolla tube | present | present | present | present |
| Flower: protusion of stigma | absent | absent | present | absent |
| Fruit cluster: density | dense | dense | dense | medium |
| *Unripe fruit: intensity of green colour | light | light | light | light |
| *Fruit: size | medium to large | medium to large | medium to large | medium to large |
| *Fruit: shape in longitudinal section | oblate | round | round | round |
| Fruit: attitude of sepals | erect | erect | erect | erect |
| Fruit: diameter of calyx basin | medium to large | medium | medium | large |
| Fruit: depth of calyx basin | medium | medium | medium | shallow |
| *Fruit: intensity of bloom | strong | strong | strong | strong |
| *Fruit: colour of skin | dark blue | dark blue | dark blue | dark blue |
| Fruit: firmness | firm | firm | firm | firm |
| *Fruit: sweetness | medium to high | low to medium | medium | medium to high |
| *Fruit: acidity | medium | medium | high | medium |
| Fruit: size of scar | small | small | small | small |
| Fruit: average weight of ripe berry (g) | 2.1 | 1.6 | 2.3 | 2.2 |
| *Time of: beginning of flowering on current year?s shoot (varieties which fruit on one-year-old and current season?s shoots only) | very early | very early to early | early to medium | very early |
| *Time of: beginning of fruit ripening on current year?s shoot (varieties which fruit on one-year-old and current season?s shoots) | very early | early | mid season | very early |

What is claimed is:

1. A new and distinct cultivar of *Vaccinium* hybrid plant named 'RIDLEY 1111', substantially as herein shown and described.

* * * * *